(12) United States Patent
Warad et al.

(10) Patent No.: US 10,836,752 B1
(45) Date of Patent: Nov. 17, 2020

(54) METHOD FOR SYNTHESIZING 1-(NAPHTHALEN-2-YLSULFONYL)-3-(THIOPHEN-2-YL) DIAZIRIDINE

(71) Applicant: QATAR UNIVERSITY, Doha (QA)

(72) Inventors: Ismail Warad, Doha (QA); Abd Daraghmeh, West Bank (PS); Mohammed Al-Nuri, West Bank (PS); Abdelkader Zarrouk, Rabat (MA); Mohammad Mousa, West Bank (PS); Anas Al-Ali, West Bank (PS); Amjad M. Shraim, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 16/838,520

(22) Filed: Apr. 2, 2020

(51) Int. Cl.
*C07D 409/04* (2006.01)

(52) U.S. Cl.
CPC .................................. *C07D 409/04* (2013.01)

(58) Field of Classification Search
CPC .................................................. C07D 409/04
See application file for complete search history.

(56) References Cited

U.S. PATENT DOCUMENTS

| 3,290,289 A | 12/1966 | Fuchs |
| 3,459,739 A | 8/1969 | Borrevang |
| 2012/0184556 A1 | 7/2012 | Conn et al. |

FOREIGN PATENT DOCUMENTS

JP   H08176103 A   7/1996

OTHER PUBLICATIONS

Lykke, L., "Catalytic asymmetric diaziridination." Journal of the American Chemical Society 135.12 (2013): 4692-4695.*
Arruje Hameed et al., "Facile and Green Synthesis of Saturated Cyclic Amines", MDPI Molecules 2017, 22, 1691; doi:10.3390/molecules22101691, www.mdpi.com/journal/molecules, 22 pages.
Rajender S. Varma, "Solvent-free Organic Synthesis, Using Suported Reagents and Microwave Irriadiation", Department of Chemistry and Texas Research Institute for Environmental Studies (TRIES), Sam Houston State University, Huntsville, Texas 77341-2117, USA, Green Chemistry, Feb. 1999, pp. 43-55.

* cited by examiner

*Primary Examiner* — John M Mauro
(74) *Attorney, Agent, or Firm* — Squire Patton Boggs (US) LLP (57) ABSTRACT

A microwave assisted method for synthesizing a diarziridine in the absence of aminating agents, by reacting a sulphonylhydrazine and an aldehyde to form a mixture and exposing the mixture to microwave radiation for a duration of time sufficient to produce a diarziridine.

18 Claims, 6 Drawing Sheets

METHOD FOR SYNTHESIZING 1-(NAPHTHALEN-2-YLSULFONYL)-3-(THIOPHEN-2-YL) DIAZIRIDINE

FIELD OF THE INVENTION

The present invention relates to a method or process for synthesizing a diaziridine, and more particularly to a microwave-assisted method or process of synthesizing the desired diaziridine from a sulfonyl hydrazine and an aldehyde.

BACKGROUND OF THE INVENTION

Diaziridines (1,2-diazacyclopropanes) are heterocyclic compounds containing two nitrogen and one carbon atoms in a strained heterocyclic three membered ring. Such heterocyclic diaziridine compounds have been reported to have important medicinal applications. For example, a diaziridine derivative and the immunosuppressant, Cyclosporine A (also known as Ciclosporin or cyclosporine) have been reported to inhibit the hepatocellular uptake of cholate, phailoidin and rifampicin in liver cell membrane. They are used as anticancer drugs, as they were shown to have moderate to good activity against the lymphocytic leukemia P388 in mice [3,4]. Diaziridines are also used as potential inactivators of P450 2B enzymes, which could be utilized for illustrating the active site topology. They are used as potential agents for the treatment of hyperuricemia and gout. Diaziridines have also been employed in the treatment of mental and neurological disorders (e.g. depressions and psychoses) as well as in photo affinity labeling. Diaziridines and diaziridine-like compounds have also displayed potential for use as high energy materials.

Despite the importance and versatility of diaziridines, there are several factors that affect its synthesis, such as starting materials, application needs, safety, cost, overall ease of the process, and purification and work-up.

Conventionally, diaziridines are prepared by the scheme (illustrated below) developed by E. Schmitz, which involves the reaction of an aldehyde (where R' is hydrogen) or ketone (where R' is $-C(R^x)_3$) with hydroxylamine-O-sulfonic acid or ammonia with a chloramine.

In view of the challenges with conventional techniques for synthesizing diaziridines, there is a need to provide an improved synthetic route to produce diaziridines that is economical, quick and safe for large-scale, commercial manufacture in an industrial setting. Such a method is provided in FIG. 1.

SUMMARY OF THE INVENTION

Embodiments of the present invention solve many of the problems and/or overcome many of the drawbacks and disadvantages of the art by providing an improved method or process for synthesizing diaziridines without the need for the use of any aminating agent as they are mostly corrosive and highly toxic.

A method for synthesizing a diaziridine in the absence of an aminating agent, comprising:
(a) contacting the sulphonylhydrazine with an aldehyde to form a mixture; and
(b) subjecting the mixture to a microwave radiation for a period of time effective to form a diaziridine.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE INVENTION

Embodiments of the present invention provide improved systems and methods for synthesizing the desired diaziridine without an aminating agent, from a sulfonyl hydrazine and an aldehyde. The processes described herein are exemplary processes only and used for illustrative purposes. Other variations and combinations of steps and components may be used as necessary.

The features, structures, or characteristics of example embodiments described throughout this specification may be combined in any suitable manner in one or more example embodiments. For example, the usage of the phrases "certain embodiments," "an example embodiment," "some embodiments," or other similar language, throughout this specification refers to the fact that a particular feature, structure, or characteristic described in connection with an embodiment may be included in at least one embodiment. Thus, appearances of the phrases "in certain embodiments," "an example embodiment," "in some embodiments," "in other embodiments," or other similar language, throughout this specification do not necessarily all refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain example embodiments, and not in limitation thereof.

As used herein, any ranges presented are inclusive of the end-points. For example, "a temperature between 10° C. and 30° C." and "a temperature from 10° C. to 30° C." include 10° C. and 30° C., as well as any temperature in between.

As used herein, aminating agents include chloramine, N-chloroalkylamines, hydroxylamine-O-sulfonic acid and their simple alkyl derivatives, but also oxaziridines unsubstituted at nitrogen.

As used herein, the term "about," when used in reference to a particular recited numerical value, means that the value may vary from the recited value by no more than 1%, 2%, 3%, 4%, or 5%. For example, in some embodiments, "about" means a variance of 1%. By way of further example, in some embodiments, "about means a variance of 2%. By way of further example, in some embodiments, "about means a variance of 3%. By way of further example, in some embodiments, "about means a variance of 4%. By way of further example, in some embodiments, "about means a variance of 5%. By way of further example, as used herein, the expression "about 100" includes 99 and 101 and all values in between (e.g., 99.1, 99.2, 99.3, 99.4, etc.).

Figure 1:
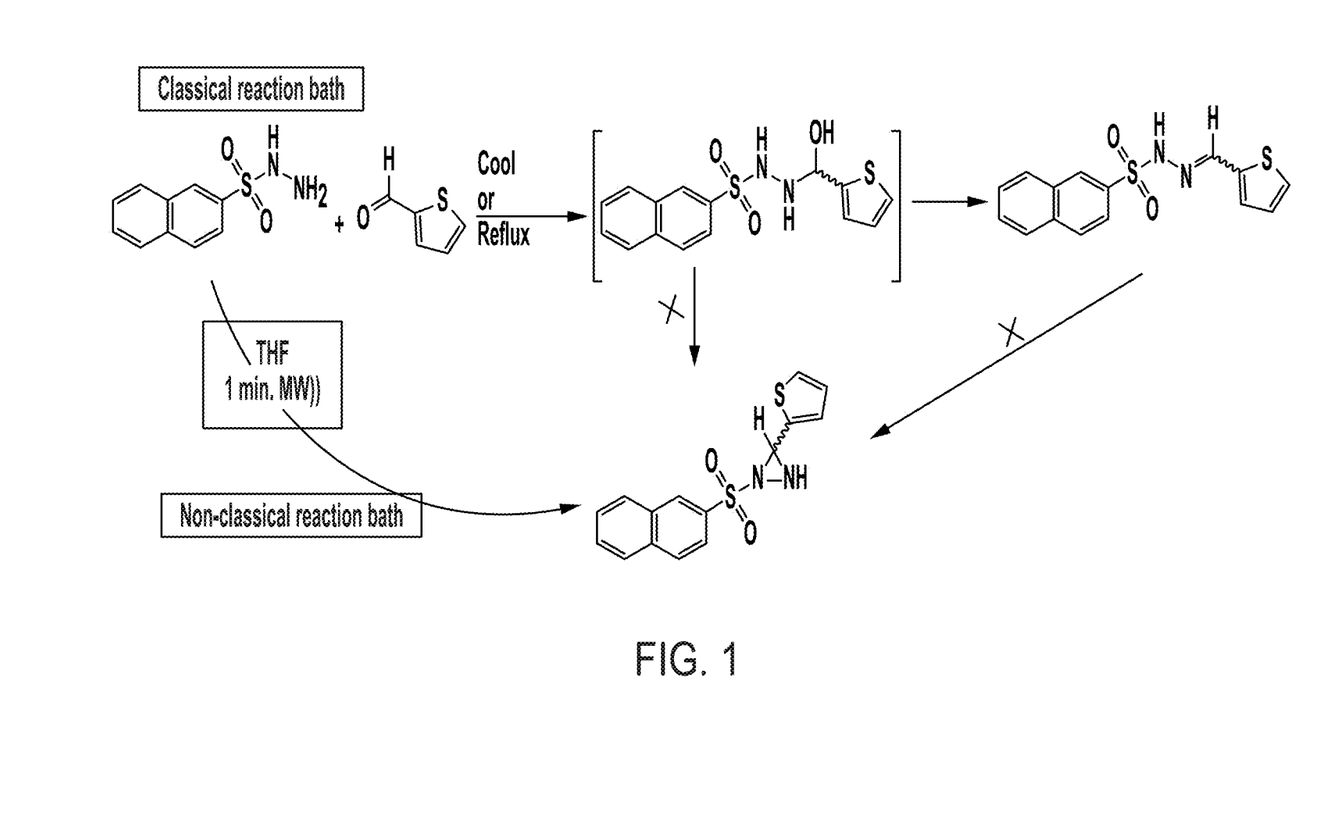
FIG. 1 shows an improved scheme for synthesizing diaziridine according to one embodiment of the invention.

FIG. 1 illustrates an improved method for synthesizing the desired diaziridine according to an embodiment. According to one embodiment, a sulfonohydrazide may be dissolved in a cyclic ether to form a mixture. In one embodiment, the sulfonohydrazide may be N'-(thiophen-2-ylmethylene)naphthalene-2-sulfonohydrazide and the cyclic ether may be tetrahydrofuran. An equivalent amount of an aldehyde may be added to the mixture. In one embodiment, the aldehyde may be 2-thiophenecarboxaldehyde. The mixture may then be exposed to microwave radiation for a duration of time effective to obtain a diaziridine. In one embodiment, the duration of time may be in a range from about 30 seconds to about 5 minutes. In one embodiment, the frequency of the microwave radiation is about 2.45 GHz. The resulting diaziridine may be dried and washed with one or more solvents to remove impurities. In one embodiment, the resulting diaziridine may be dried with a rotary evaporator. In some alternative, the temperature of the rotary evaporator may be up to 80° C. to remove tetrahydrofuran from the resulting material. In another embodiment, the one or more solvents may be an organic solvent, and inorganic solvent or combinations thereof. In some alternative, the organic solvent may be n-Hexane and the inorganic solvent may be water.

In some or any embodiments the method comprises dissolving or suspending the sulphonylhydrazine in a solvent before it is contacted with the aldehyde. In some or any embodiments, the solvent is a cyclic ether. In some or any embodiments, the solvent is tetrahydrofuran (THF). In some embodiments, the solvent may be any conventional replacements for THF, including Diethyl ether, 2-Methyltetrahydrofuran or green (environmental) replacements for THF, such as Cyclopentyl methyl ether.

In some or any embodiments, the method, further comprising a step c) wherein one or more aqueous solutions and a second solvent are added to the diaziridine. In some or any embodiments, the second solvent comprises n-hexane. In some or any embodiments, the second solvent is n-hexane.

In some or any embodiments, the molar ratio of sulphonylhydrazine to aldehyde is about 1:1, about 1:1.05, about 1:1.1, about 1:1.15, about 1:1.2, about 1:1.25, or about 1:1.3. In some or any embodiments, the molar ratio of sulphonylhydrazine to aldehyde is about 1:1. In some or any embodiments, the molar ratio of sulphonylhydrazine to aldehyde is about 1:1.05. In some or any embodiments, the molar ratio of sulphonylhydrazine to aldehyde is about 1:1.1. In some or any embodiments, the molar ratio of sulphonylhydrazine to aldehyde is about 1:1.15. In some or any embodiments, the molar ratio of sulphonylhydrazine to aldehyde is about 1:1.2. In some or any embodiments, the molar ratio of sulphonylhydrazine to aldehyde is about 1:1.25. In some or any embodiments, the molar ratio of sulphonylhydrazine to aldehyde is about 1:1.3.

In a further embodiment, the path of the dehydration reaction for the improved method may change from a classical Schiff base into a diaziridine heterocyclic path by controlling the reaction conditions.

In another embodiment, a novel diaziridine may be synthesized in one pot with an excellent yield, very short time, and with no side products under microwave radiation starting from a hydrazide reagent.

In some or any embodiments, the sulphonylhydrazine is according to the following formula:

where $Ar^1$ is an aryl group, as defined herein. In some or any embodiments, the sulphonylhydrazine comprises the following formula:

In some or any embodiments, the sulphonylhydrazine is according to the following formula:

In some or any embodiments, the aldehyde is according to the following formula:

where $Ar^2$ is an aryl group, as defined herein. In some or any embodiments, the aldehyde comprises the following formula:

In some or any embodiments, the aldehyde is according to the following formula:

In some or any embodiments, the diaziridine is according to the following formula:

where $Ar^1$ is an aryl group, as defined herein, and $Ar^2$ is a heteroaryl group, as defined herein. In some or any embodiments, including any embodiments in this paragraph, $Ar^1$ comprises naphthyl. In some or any embodiments, including any embodiments in this paragraph, $Ar^1$ is unsubstituted naphthyl. In some or any embodiments, including any embodiments in this paragraph, $Ar^2$ comprises thienyl. In some or any embodiments, including any embodiments in this paragraph, $Ar^2$ is unsubstituted thienyl. In some or any embodiments, including any embodiments in this paragraph, the diaziridine is according to the following formula:

In some or any embodiments, including any embodiments in this paragraph, the diaziridine is according to the following formula:

In some of any embodiments, including any embodiments in this paragraph, the diaziridine is according to the following formula:

The term "alkyl," as used herein, means a linear or branched hydrocarbon group having one to eight carbon atoms, in some embodiments, one to six carbon atoms. In some embodiments, alkyl is methyl, ethyl, propyl, isopropyl, butyl, s-butyl, t-butyl, isobutyl, pentyl, hexyl and the like.

The term "aryl," as used herein, means a monovalent six- to fourteen-membered, mono- or bi-carbocyclic ring, wherein each ring is aromatic. In some or any embodiments, aryl comprises phenyl. In some or any embodiments, aryl comprises naphthyl. In some or any embodiments, aryl is phenyl. In some or any embodiments, aryl is naphthyl.

The term "heteroaryl," as used herein, means a monocyclic, or fused bicyclic, monovalent aromatic ring radical of 5 to 14 ring atoms containing one or more heteroatoms (in some embodiments, one, two, three, or four ring heteroatoms) independently selected from —O—, —S—, —N—, and —N($R^x$)—, where the remaining ring atoms are carbon and where $R^x$ is hydrogen or alkyl. Unless stated otherwise, the point of attachment may be located on any atom of any ring of the heteroaryl group, valency rules permitting. In particular, when the point of attachment is located on the nitrogen, $R^x$ is absent. More specifically, the term heteroaryl includes, but is not limited to, 1,2,4-triazolyl, 1,3,5-triazolyl, pyridinyl, pyrrolyl, imidazolyl, thienyl, furanyl, indolyl, isoindolyl, benzimidazolyl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, pyrrolo[3,2-c]pyridinyl (including, for example, pyrrolo[3,2-c]pyridin-2-yl or pyrrolo[3,2-c]pyridin-7-yl, and the like), thiazolyl, isothiazolyl, thiadiazolyl, benzothiazolyl, and benzothienyl. In some or any embodiments, heteroaryl is a 5 or 6-membered ring. In some or any embodiments, heteroaryl is thienyl.

The following example, which describes a procedure carried out on a laboratory scale, allows for a better understanding of certain embodiments. This example should not, however, be regarded as limiting and the sulfonyl hydrazine reactant and/or the aldehyde can be modified without departing from the scope of the invention.

Example 1—1-(naphthalen-2-ylsulfonyl)-3-(thiophen-2-yl)diaziridine 2.22 g (10.0 mmol) of naphthalene-2-sulfonohydrazide was dissolved in approximately 40 mL of tetrahydrofuran to form a reaction mixture in a conventional crucible. Approximately 1.2 g (11 mmol) of 2-thiophenecarboxaldehyde was added to the reaction mixture, with stirring or agitation. The conventional crucible containing the reaction mixture was placed in a microwave oven under a hood operating at 2.45 GHz, 1 KW power, for 5 minutes, during which no change in color was observed. The reaction mixture was left on a surface under atmospheric conditions for approximately 10 minutes to cool down to room temperature. The reaction mixture exhibited a light white turbidity. The resulting material was then transferred to a rotary evaporator operating at 60° C. up to 80° C. to remove tetrahydrofuran from the resulting material. The resulting material was washed with 60 mL of n-hexane and water to remove additional impurities. The resulting material in the n-hexane layer was subsequently dried and weighed. The weight of the resulting material was approximately 2.85 g (9.00 mmol) of 1-(naphthalen-2-ylsulfonyl)-3-(thiophen-2-yl)diaziridine (yield was approximately 90%).

Figure 2:
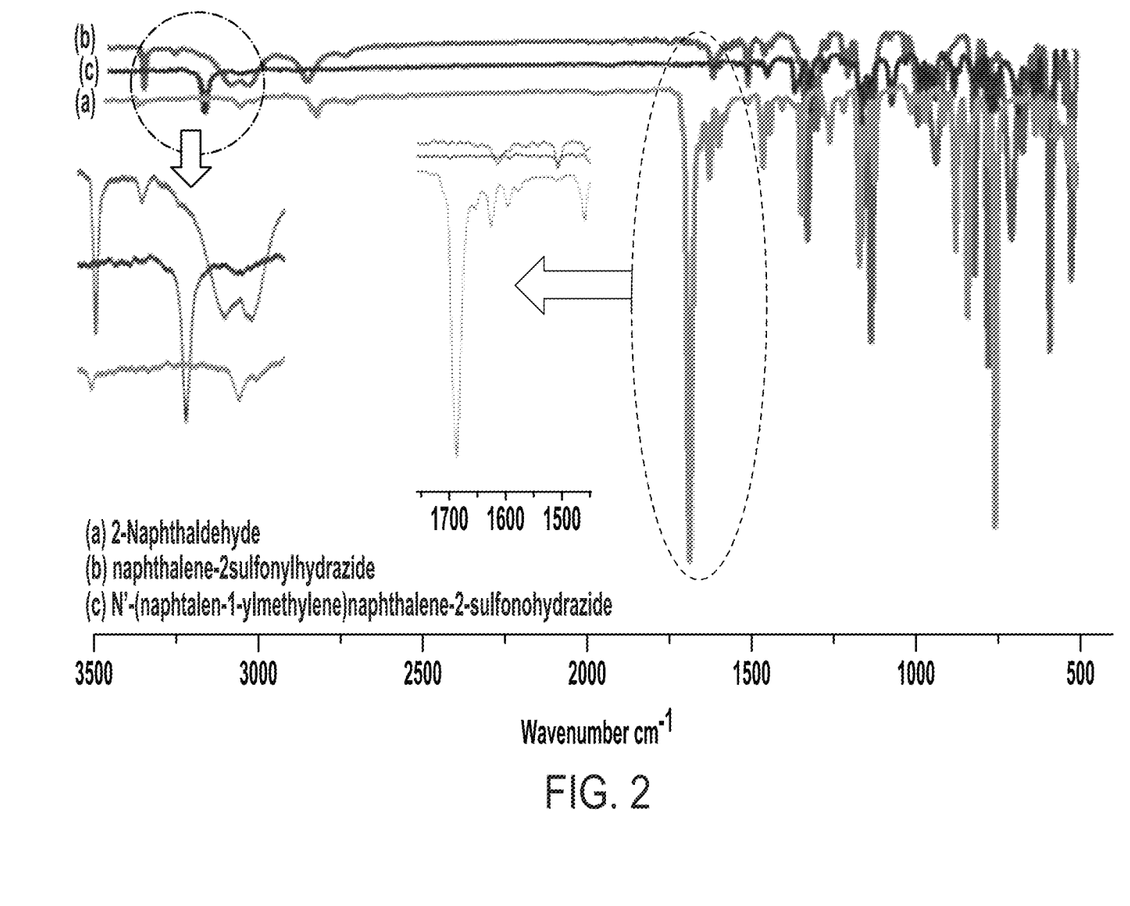
FIG. 2 illustrates an infrared spectra of diaziridine sample and their reagents, according to an embodiment.

As shown in FIG. 2, the IR-spectra of the sample produced in EXAMPLE 1 indicates that the vibration frequencies of each functional group appeared at their expected positions. The disappearance of the C=O aldehyde carbonyl and amine of hydrazine groups confirmed the dehydration of one water molecule from the starting material when they combined together. The appearance of the main stretching vibration bands in the product's spectrum is consistent with its structural formula. It is obvious that the broad $v_{(NH)}$ band at 3320 cm$^{-1}$ is shifted to 3200 cm$^{-1}$, $v_{(C-H)}$ aromatic vibration at 3120 cm$^{-1}$ is shifted to 3040 cm$^{-1}$. Moreover, $v_{(C=O)}$ band at 1680 cm$^{-1}$ disappeared.

Figure 3:
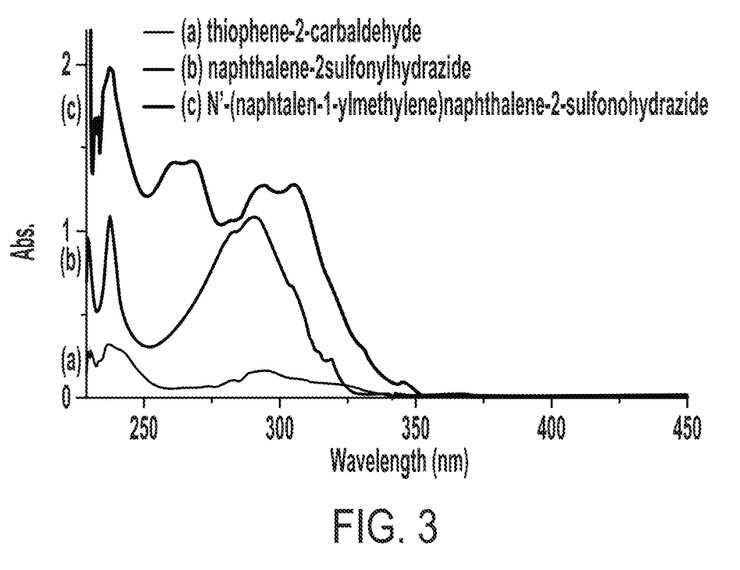
FIG. 3 illustrates an ultraviolet-visible spectra of diaziridine sample and their reagents in methanol, according to an embodiment.

The UV-Vis. Spectra of the reagents and sample produced in EXAMPLE 1 recorded in methanol as shown in FIG. 3, indicates that completeness of the reaction was supported by ($\pi \rightarrow \pi^*$)/($n \rightarrow \pi^*$) UV absorption changes at $\lambda_{max}$=235, 275, 315, and 385 nm. No peak above 400 nm was detected.

Figure 4:
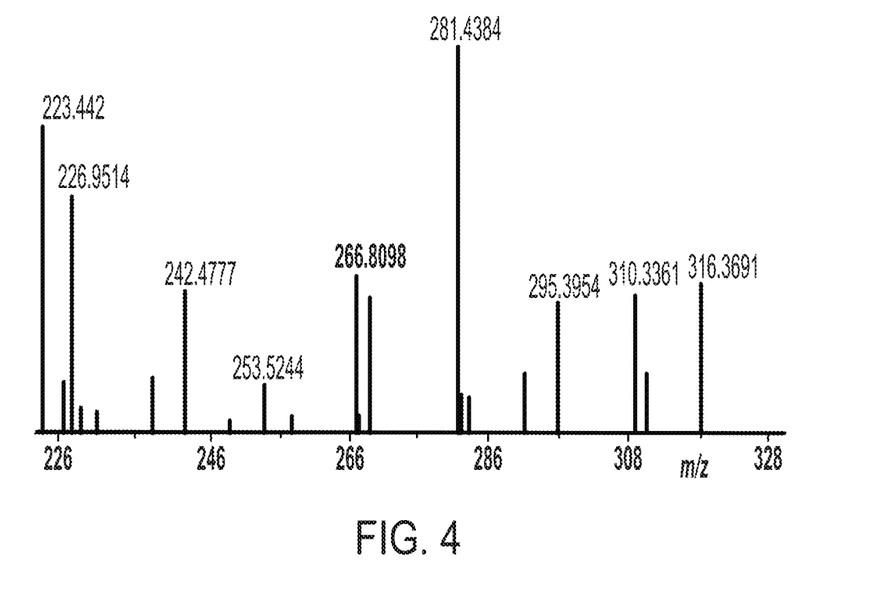
FIG. 4 illustrates the Gas Chromatography Mass Spectrometry (GC/MS) molecular ion weight of diaziridine sample, according to an embodiment.

The GC/MS mass spectra of the sample produced in EXAMPLE 1 as shown in FIG. 4, indicates a molecular ion peak, [M+] m/z=316.8, which is agreement with expected theoretical molecular weight of 316.2

Figure 5:
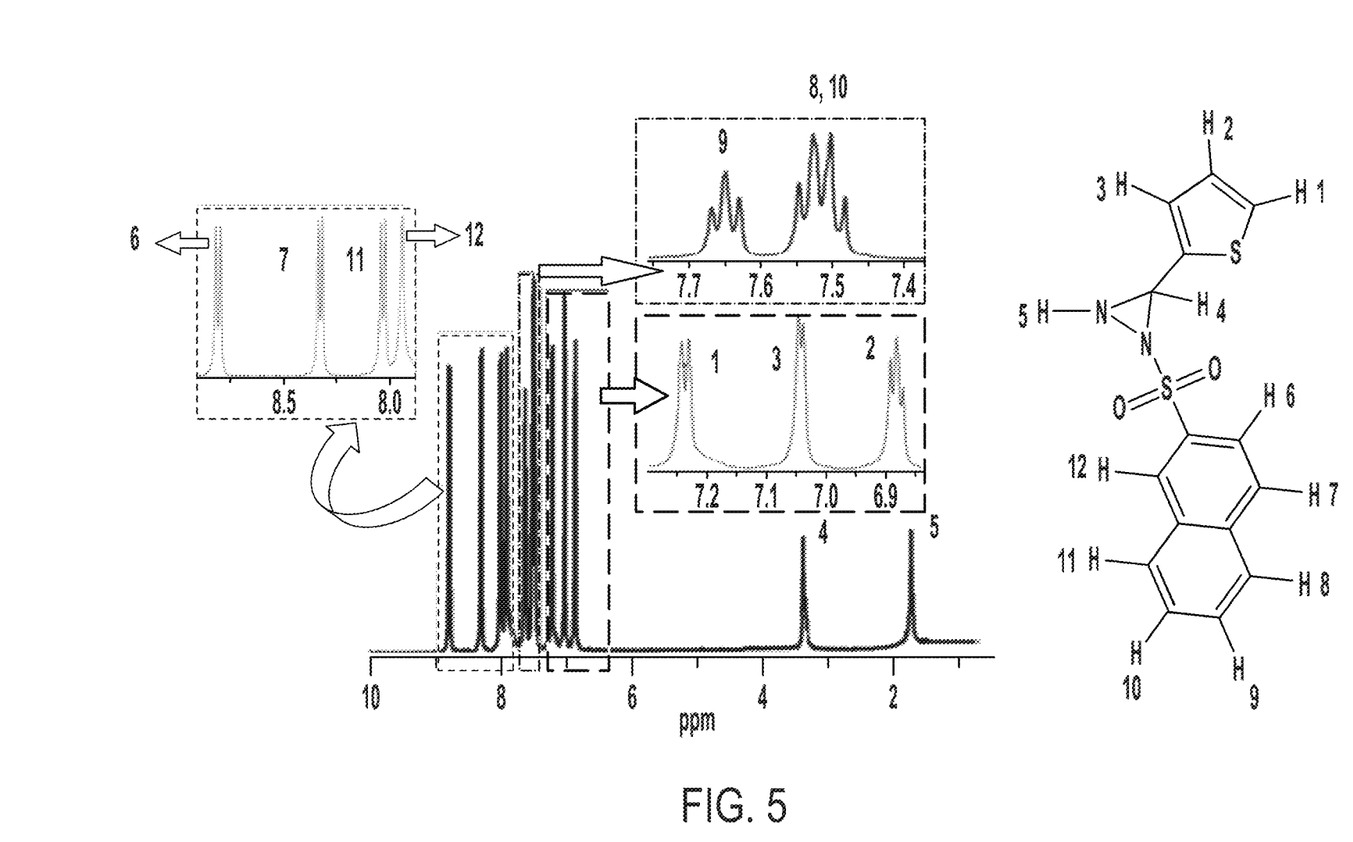
FIG. 5 illustrates the Nuclear Magnetic Resonance (NMR) analysis of diaziridine sample, according to an embodiment.

The 1H Nuclear Magnetic Resonance (NMR) spectra of the sample produced in EXAMPLE 1 performed in CDCl$_3$, as shown in FIG. 5, identifies two signals of aliphatic protons, detected at 0.8 ppm for CH and 3.2 ppm for NH. Ten signals related to the aromatic protons were also observed at 6.8-9.0 ppm. The chemical shifts were assigned to their positions directly on the spectrum.

The TG/DTA analysis of the sample produced in EXAMPLE 1, was performed at a heat rate of 10 min/° C. and the sample was found to be stable up to 200° C. and decomposed in one step process.

Figure 6:
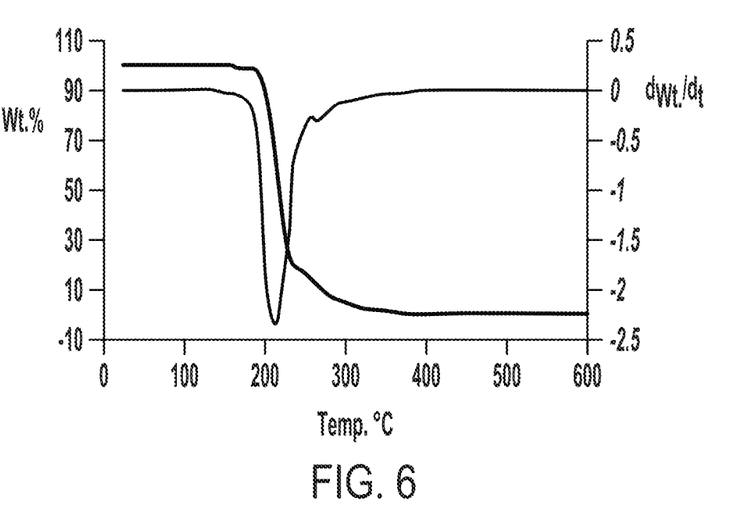
FIG. 6 illustrates the Thermogravimetry/Differential Thermal Analysis (TG/DTA) analysis of diaziridine sample, according to an embodiment.

As shown in FIG. 6, the sample produced in EXAMPLE 1, was analyzed utilizing Density Functional Theory calculations to identify the optimized structures of the sample including its e-rich O, S, N, naphthalene and thiophene functional groups with 3-membered ring N—N—C cyclic unit.

The foregoing description of the exemplary embodiments has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

The invention claimed is:

1. A method for synthesizing a diaziridine in the absence of aminating agents, comprising:
    (a) contacting a sulphonylhydrazine with an aldehyde to form a mixture; and
    (b) subjecting the mixture to a microwave radiation for a period of time effective to form a diaziridine.

2. The method of claim 1, wherein the sulphonylhydrazine is dissolved or suspended in a first solvent.

3. The method of claim 2, wherein the first solvent is a cyclic ether.

4. The method of claim 2, wherein the first solvent is tetrahydrofuran.

5. The method of claim 1, wherein the sulphonylhydrazine is naphthalene-2-sulfonohydrazide.

6. The method of claim 1, wherein the aldehyde is 2-thiophenecarboxaldehyde.

7. The method of claim 2, wherein the first solvent is removed after forming the diaziridine.

8. The method of claim 2, wherein the first solvent is removed by rotary evaporation at a first bath temperature.

9. The method of claim 8, wherein the first bath temperature is about 80 degrees Celsius.

10. The method of claim 1, wherein the diaziridine is 1-(naphthalen-2-ylsulfonyl)-3-(thiophen-2-yl)diaziridine.

11. The method of claim 1, wherein the frequency of the microwave radiation is about 2.45 GHz.

12. The method of claim 1, wherein the period of time is in the range of about 30 seconds to about 5 minutes.

13. The method of claim 1, further comprising a step c) wherein water or one or more aqueous solutions and a second solvent are added to the diaziridine forming a first layer comprising the diaziridine and a second layer without the diaziridine.

14. The method of claim 13, wherein the one or more aqueous solutions is water.

15. The method of claim 13, wherein the second solvent comprises n-hexane.

16. The method of claim 13, wherein the second solvent is n-hexane.

17. The method of claim 13, wherein the layer comprising the diaziridine is dried.

18. The method of claim 13, wherein the diaziridine is isolated in about 30 minutes counting from the beginning of step c).

* * * * *